United States Patent [19]
Sunshine et al.

[11] Patent Number: 4,962,124
[45] Date of Patent: Oct. 9, 1990

[54] ONSET-HASTENED/ENHANCED ANTIPYRETIC RESPONSE

[75] Inventors: Abraham Sunshine, New York; Eugene M. Laska, Larchmont, both of N.Y.

[73] Assignee: Analgesic Associates, Larchmont, N.Y.

[21] Appl. No.: 398,482

[22] Filed: Aug. 25, 1989

Related U.S. Application Data

[63] Continuation-in-part of Ser. No. 121,849, Nov. 17, 1987, Pat. No. 4,868,214.

[51] Int. Cl.⁵ .............................................. A61K 31/19
[52] U.S. Cl. .................................. 514/568; 514/570; 514/557; 514/947; 514/960; 514/962
[58] Field of Search ............... 514/570, 568, 557, 960, 514/962, 947

[56] References Cited

U.S. PATENT DOCUMENTS 4,555,524 11/1985 Gruber et al. ...................... 514/570
4,690,823 9/1987 Lohner et al. ...................... 514/570

Primary Examiner—Jacqueline V. Howard
Attorney, Agent, or Firm—Burns, Doane, Swecker & Mathis

[57] ABSTRACT

Onset-hastened and enhanced antipyretic response is elicited in a human mammal in need of such treatment, i.e., a human mammal suffering from elevated body temperature (fever), by administering thereto a unit dosage onset-hastening/enhancing antipyretically effective amount of the S(+) ketoprofen enantiomer, said enantiomer being substantially free of its R(−) ketoprofen antipode.

24 Claims, No Drawings

ONSET-HASTENED/ENHANCED ANTIPYRETIC RESPONSE

CROSS-REFERENCE TO RELATED APPLICATION

This is a continuation-in-part of our application, Ser. No. 07/121,849, filed Nov. 17, 1987, U.S. Pat. No. 4,868,214 hereby expressly incorporated by reference and relied upon.

CROSS-REFERENCE TO COMPANION APPLICATION

Our copending application, Ser. No. 07/356,850, filed May 25, 1989.

BACKGROUND OF THE INVENTION

1. Field of the Invention

The present invention relates to the use of S(+) ketoprofen to elicit an onset-hastened and enhanced antipyretic response in human mammalian organisms in need of such treatment, and to certain pharmaceutical compositions comprising unit dosage effective amounts of S(+) ketoprofen.

2. Description of the Art

Ketoprofen, also known as DL-2-(3-benzoylphenyl)-propionic acid, has the structural formula

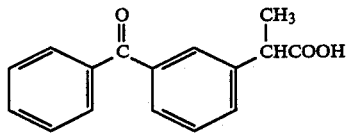

The compound is well-known as a nonsteroidal anti-inflammatory drug having analgesic and antipyretic activity. In the United States, ketoprofen is marketed under the tradename Orudis ®. Other tradenames or codenames include RP 19583, Alrheumat, Alrheumun, Capisten, Fastum, Iso-K, Kefenid, Ketopron, Lertus, Meprofen, Oruvail and Profenid. As Orudis ®, the drug is available by prescription in the U.S. as capsules containing 25 mg, 50 mg or 75 mg of ketoprofen, indicated for the acute or long-term treatment of the signs and symptoms of rheumatoid arthritis or osteoarthritis. Orudis ® is recommended at a daily dose of 150 to 300 mg, divided in three or four doses. It is recommended that drug treatment begin at 75 mg three times or 50 mg four times a day. Small people may need smaller doses. Daily dosages should not exceed 300 mg per day. See also *Physician's Desk Reference*, 41st edition, 1987, publisher Edward R. Barnhart, Medical Economics Company, Inc., Oradell, N.J. 07649, pp. 2179-2181. For mild to moderate pain and dysmenorrhea, a dose of 25 mg to 50 mg every 6 to 8 hours as needed was recently approved by the Food and Drug Administration ("F.D.A.").

As is apparent from its chemical nomenclature, ketoprofen is a racemic mixture. It is only the racemic mixture which has in fact ever been marketed. There have, however, been a few studies of the individual S(+) and R(−) isomers reported in the literature.

The prior art groups the 2-arylpropionic acids together as a class. These possess a chiral center at the carbon atoms alpha to the carboxyl function. According to the prior art, many 2-arylpropionic acids are believed to have a metabolic chiral inversion of their asymmetric center, with partial or complete conversion in nonhuman mammals of the R to the S isomer. The rate and extent of that conversion has been known to vary as noted by Hutt et al, *J. Pharm. Pharmacol.*, 35, 693-704 (1983). This metabolic inversion of the chiral center, with no other covalent change to the drug, is thus far unique to the 2-arylpropionic acids. Cadwell et al., "The Metabolic Inversion and Dispositional Enantioselectivity of the 2-Arylpropionic Acids and their Biological Consequences", *Biochem. Pharmacol.*, 37, 105-114 (1988).

Generally, if an optically active compound has two isomers, there is an argument for resolving what is believed to be the optically active and therapeutically desirable isomer. However, many of the 2-arylpropionic non-steroidal anti-inflammatory drugs (NSAIDs) are unique and run contrary to that argument because of the teachings of the prior art relating to the conversion of the R(−) to the S(+) isomer. Thus, the argument for resolving the 2-arylpropionic acids to improve their clinical effect is not as clear as with other classes of racemic drugs. In many instances, the prior art actually teaches away from such a resolution by leading one of ordinary skill in the art to believe that there would be clinical or near clinical equivalence between the S(+) form and the racemic mixture. That is, the conversion of the R(−) isomer to the S(+) form is believed to progress at such a rate and to such an extent that a substantially equivalent clinical effect would result.

The majority of the prior art was too inconclusive to yield an accurate estimate of the extent of the possible conversion of the R(−) to the S(+) form of ketoprofen in man. Moreover, among the members of that class of NSAID's, comparatively few studies appear to have been conducted on ketoprofen. However, conversion in man would be assumed by one of ordinary skill in the art since in addition to the ketoprofen specific evidence from studies cited in the specification, several members of the 2-arylpropionic acid classes of NSAID's, e.g., ibuprofen, were known to undergo substantial chiral inversion of the R to the S enantiomer in man.

Indeed, Hutt et al concluded that there was no advantage in administering the pure S(+) form of ketoprofen since a rapid in vivo conversion of the R(−) in the racemic mixture to the S(+) form would be expected, based on the fact that ketoprofen has a chiral center and it is known to be incorporated into triglycerides.

> Ketoprofen, like fenoprofen, has been reported to be incorporated into triglycerides, and, in addition, a study using [³H-α-methyl] drug in man found increasing quantities of circulating radioactivity due to tritiated water. One means of loss of ³H from the α-methyl group would be that proposed for the loss of deuterium from d₄-ibuprofen during the chiral inversion process.

Hutt et al, "Review - The Metabolic Chiral Inversion of 2-Arylpropionic Acids - A Novel Route with Pharmacological Consequences," *J. Pharm. Pharmacol.*, Vol. 351, pp. 693-674 at 703 (1983). Thus, Hutt et al recognized that evidence existed supporting chiral inverion of the R(−) to the S(+) isomer for ketoprofen.

It has recently been noted that contrary to the expectations of the prior art, there is no conversion of R(−) to S(+) ketoprofen in man.

> Interestingly, the R-enantiomer of some of these agents (e.g., ibuprofen, fenoprofen, and benoxaprofen) may undergo a unique in vivo irreversible inversion to the S-enantiomer. This inversion is not a universal occurrence, as, at least in humans, it does not occur to any significant extent with tiaprofenic acid, indoprofen, carprofen, and perhaps ketoprofen.

Jamali et al, "Stereoselective Pharmacokinetics of Flurbiprofen in Humans and Rats," *Journal of Pharmaceutical Sciences*, Vol. 77, No. 8, pp. 666–69 (August 1988).

In summary, the current state of the art now teaches that there is no conversion of R(−) to S(+) ketoprofen in humans and that the S(+) form is the active enantiomer of ketoprofen. However, there do not appear to be any human experiments on the efficacy of the separate enantiomers reported in the literature. The prior art, moreover, is conspicuously silent in respect to any onset-hastened/enhanced alleviation of mammalian fever utilizing whatever form of the ketoprofen drug species.

SUMMARY OF THE INVENTION

Surprisingly, the present inventors now find that S(+) ketoprofen can be advantageously administered to mammals suffering from elevated body temperature, especially humans, to not only elicit a more potent antipyretic response but also to evoke such response more rapidly than possible by administration of the same dose of ketoprofen in its racemic form.

This is particularly surprising in light of the art's failure to even investigate the activity in vivo for S(+) ketoprofen versus the R(−) isomer and the racemic mixture, far less the art's failure to make telling observations of the fever level or amount of relief at meaningful time points sufficiently soon after dosing in an appropriate antiypyretic model.

In one aspect, the present invention thus provides a method of hastening the onset of antipyretic response in a human mammal, said method comprising administering to a human mammal in need of such treatment an effective onset-hastening antipyretic amount of S(+) ketoprofen substantially free of R(−) ketoprofen.

In another aspect, the present invention provides a method of eliciting an enhanced antipyretic response in a mammal, particularly shortly after dosing, said method comprising administering to a mammal in need of such treatment an effective antipyretic enhancing amount of S(+) ketoprofen substantially free of R(−) ketoprofen.

In yet another aspect, the present invention provides a pharmaceutical composition of matter for use in eliciting an onset hastened and enhanced antipyretic response in mammals, especially humans, said composition comprising an effective antipyretic unit dosage amount of S(+) ketoprofen substantially free of R(−) ketoprofen. Typically, S(+) ketoprofen is associated with a nontoxic pharmaceutically acceptable inert carrier or diluent therefor.

DETAILED DESCRIPTION OF THE PREFERRED EMBODIMENTS OF THE INVENTION

The term "ketoprofen" or "racemic ketoprofen" as used herein is intended to encompass not only DL-2-(3-benzoylphenyl)propionic acid itself but also any pharmaceutically acceptable salt thereof.

The term "S(+) ketoprofen" as used herein is intended to encompass not only the dextrorotatory or S(+) isomer of 2-(3-benzoylphenyl)propionic acid but also any pharmaceutically acceptable, antipyretically effective salt thereof. The expression "substantially free of R(−) ketoprofen" as used in conjunction with the term "S(+) ketoprofen" means that the S(+) ketoprofen is sufficiently free of R(−) ketoprofen [which is the levorotatory form or R(−) isomer of 2-(3-benzoylphenyl)-propionic acid or salt thereof] to exert the desired onset-hastened and enhanced antipyretic effect. Practically speaking, this means that the active ingredient should contain at least 90% by weight S(+) ketoprofen and 10% or less by weight R(−) ketoprofen. Preferably, the weight ratio of S(+) ketoprofen to R(−) ketoprofen is greater than or equal to 20:1, more preferably greater than 97:3. Ideally, the S(+) ketoprofen is 99 or more % by weight free of R(−) ketoprofen, i.e., the weight ratio of S to R is approximately equal to or greater than 99:1. At the present time, a 20:1 ratio of S(+) to R(−) is readily obtainable from racemic ketoprofen by literature methods and eminently useful in the practice of the present invention.

Where specific amounts of S(+) ketoprofen are set forth below, it should be understood that, unless otherwise specified, the amounts are given in mg of the acid, not of a salt. Moreover, unless otherwise specified, for simplicity's sake the amounts given represent total ketoprofen content, most of which is in the S(+) form. For example, "50 mg S(+) ketoprofen" means 50 mg total ketoprofen at least 90% of which is in the S(+) form, preferably at least 95%.

S(+) ketoprofen, in accord with the present invention, produces the following unexpected results:

(1) the antipyretic effect of ketoprofen on the mammal is brought on more quickly than by use of the same dose of racemic ketoprofen; and (2) a greater antipyretic response is elicited in the early hours than is elicited by the same dose of racemic ketoprofen.

These unexpected results can be achieved in the treatment of fever responsive to an NSAID (non-steroidal anti-inflammatory drug). This includes the fever associated with respiratory infections such as colds and flu.

For patients suffering from such elevated body temperature, who require treatment at a particular dose of racemic ketoprofen, the time from administration of medication to the onset of effective relief is clearly of paramount importance. The present inventors' discovery that S(+) ketoprofen, when used in place of racemic ketoprofen at the same dose, substantially shortens the onset time (i.e., substantially hastens the onset) of antipyretic response is therefore very significant. It is likewise quite unexpected.

In a group responsive to a given dose of the racemate, it is believed that onset time for antipyretic response can be reached, on the average, about one-third sooner when S(+) ketoprofen is used rather than when racemic ketoprofen is administered, depending on the dose level and the intensity of the fever, but particularly at the low end (6.0 to 50 mg) of the antipyretic dosage range and for patients with moderate fever.

Insofar as concerns enhanced antipyretic response, more pronounced fever reduction is obtained when S(+) ketoprofen is used at the same dose level as racemic ketoprofen, especially during the first few hours.

The precise amount of S(+) ketoprofen for use in accord with the present invention will vary depending, for example, on the size and kind of the mammal and the condition for which the drug is administered. For use in humans, the antipyretically effective amount of S(+) ketoprofen will typically be from about 6.0 to 75 mg, although greater amounts (e.g. 100 mg) may be employed if needed for fever reduction relief and if tolerated by the patient. The daily dose in humans preferably will not exceed 300 mg S(+) ketoprofen, although greater amounts could be employed if tolerated by the patient. Preferred unit dosage compositions for use in the treatment of slight to moderate fever contain 6.0, 12.5, 25, 50 or 75 mg S(+) ketoprofen.

While the compositions for use in the invention are preferably for oral use, they may also be formulated for and administered by other routes which are known for administering antipyretic drugs, e.g., as suppositories or parenteral solutions, or as topical formulations such as ointments, gels, creams, lotions, solutions, impregnated bandages or other topical delivery devices, and so forth. Also, it should be noted that the preferred human dosage levels indicated above are for use in adults; pediatric compositions would contain proportionately less of the active ingredient.

The compositions for use herein are very conveniently administered to mammals by any route of administration suitable for racemic ketoprofen, e.g. oral, rectal, topical or parenteral. Preferably S(+) ketoprofen is formulated with any suitable nontoxic pharmaceutically acceptable inert carrier material. Such carrier materials are well known to those skilled in the art of pharmaceutical formulations. For those not skilled in the art, reference is made to the text entitled *Remington's Pharmaceutical Sciences*, 17th edition, 1985, ed. Alfonso R. Gennaro, Mack Publishing Company, Easton, Pa. 18042. In a typical preparation for oral administration, e.g. tablet, capsule or caplet, S(+) ketoprofen in an effective antipyretic amount and substantially free of R(−) ketoprofen, is combined with any oral nontoxic pharmaceutically acceptable inert carrier such as lactose, starch (pharmaceutical grade), dicalcium phosphate, calcium sulfate, kaolin, mannitol and powdered sugar. Additionally, when required, suitable binders, lubricants, disintegrating agents and coloring agents can also be included. Typical binders include starch, gelatin, sugars such as sucrose, molasses and lactose, natural and synthetic gums such as acacia, sodium alginate, extract of Irish moss, carboxymethylcellulose, methylcellulose, polyvinylpyrrolidone, polyethylene glycol, ethylcellulose and waxes. Typical lubricants for use in these dosage forms can include, without limitation, boric acid, sodium benzoate, sodium acetate, sodium chloride, leucine and polyethylene glycol. Suitable disintegrators can include, without limitation, starch, methylcellulose, agar, bentonite, cellulose, wood products, alginic acid, guar gum, citrus pulp, carboxymethylcellulose and sodium lauryl sulfate. If desired, a conventional pharmaceutically acceptable dye can be incorporated into the dosage unit form, i.e., any of the standard FD&C dyes. Sweetening and flavoring agents and preservatives can also be included, particularly when a liquid dosage form is formulated, e.g. an elixir, suspension or syrup. Also, when the dosage form is a capsule, it may contain, in addition to materials of the above type, a liquid carrier such as a fatty oil. Various other materials may be present as coatings or to otherwise modify the physical form of the dosage unit. For instance, tablets, pills or capsules may be coated with shellac and/or sugar. Such compositions should preferably contain at least 0.1% of S(+) ketoprofen; generally, S(+) ketoprofen will be from about 2% to about 60% of the weight of the unit. Typical unit dosage forms for oral administration will contain about 6.0 to 75 mg, preferably 25 to 50 mg, S(+) ketoprofen, if formulated for immediate release, as is preferred. If the composition is intended for sustained release, much larger amounts of the active ingredient would of course be incorporated into an individual unit; in such case, at least 6.0, and preferably up to 50 or 75 mg of the total amount of S(+) ketoprofen, should be formulated for immediate release so as to obtain the desired degree of enhanced antipyretic response and hastened onset.

A typical capsule for oral administration may contain, in addition to the selected amount of S(+) ketoprofen, the following combination of inactive ingredients/carrier materials: D&C Yellow 10, FD&C Blue 1, FD&C Yellow 6, gelatin, lactose, magnesium stearate and titanium dioxide.

Moreover, the compositions for use in obtaining enhanced antipyretic response and hastened onset in accord with the present invention may, in addition to the selected dose of S(+) ketoprofen, also contain other active ingredients and/or enhancing agents. Thus, for example, S(+) ketoprofen may be combined with such ingredients and agents as have been described for combination with racemic ketoprofen, e.g., caffeine or other xanthine derivative, a narcotic analgesic (with or without caffeine), a skeletal muscle relaxant, an antihistamine, decongestant, cough suppressant and/or expectorant. See, for example, Sunshine et al U.S. Pat. No. 4,486,436, issued Dec. 4, 1984; Sunshine et al U.S. Pat. No. 4,552,899, issued Nov. 12, 1985; Sunshine et al U.S. Pat. No. 4,567,183, issued Jan. 28, 1986; and Sunshine et al U.S. Pat. No. 4,619,934, issued Oct. 28, 1986; and Sunshine et al pending U.S. patent application Ser. No. 815,502, filed Jan. 2, 1986.

To establish the efficacy of the compositions of this invention in humans, patients with moderate to high fever requiring an oral antipyretic agent, can be administered S(+) ketoprofen or racemic ketoprofen. To determine antipyretic efficacy, the temperature of the patients is taken at different intervals of time and evaluated/compared. Appropriate statistical methods, including survival analysis, can be used to show that the S(+) enantiomer has shorter onset and is more efficacious (Laska, E., Gormely, M., Sunshine, A., Belleville, J. W., Kantor, T., Forrest, W. H., Siegel, C. and Meisner, M., "A Bioassay Computer Program for Analgesic Clinical Trials," *Clin. Pharmacol. Ther.*, 8:658, 1967; Cox, D. R., "Regression Models and Life Tables," *Journal Royal Statistical Society*, Series B, Volume 34:187–202, 1972).

S(+) ketoprofen for use in the method and compositions of the present invention can be prepared by a variety of methods, such as by resolution of racemic ketoprofen.

Farge et al, U.S. Pat. No. 3,641,127 describes the preparation of racemic ketoprofen and related compounds; see, in particular, Example V thereof. The Farge et al patent also describes a method for preparing the individual D- and L-isomers by oxidation of the corresponding optically active (3-benzylphenyl)alkanoic acids; see column 3, lines 22–40.

Abas et al, *J. Pharmacol. Exp. Ther.* 240(2), 637–641 (1987), have resolved racemic ketoprofen using a modification of the method of Blazevic et al, *Acta Pharmacol. Jugoslav.* 25, 155–164 (1975). Abas et al prepared the diastereoisomeric amides of R(−) and S(+) ketoprofen with (+)-R-1-methylbenzylamide from racemic ketoprofen, via the acid chlorides using thionyl chloride. The diastereoisomeric amides were separated by the HPLC (high performance liquid chromatographic) method of Sallustio et al, *Journal of Chromatography* 374, 329–337 (1986), but using a 7.8 mm×300 mm preparative column. The pure amides were then separately converted to nitroso derivatives with dinitrogen tetroxide, and the nitroso derivatives were thermally decomposed to the respective ketoprofen enantiomers as described by Balzevic et al. Purification of the R and S enantiomers by silica gel chromatography, recrystallization from diethyl ether/cyclohexane and HPLC analysis according to Sallustio et al's method afforded the R and S enantiomers with enantiomeric purities of 98% and 95%, respectively.

HPLC methods other than Sallustio et al's for resolving enantiomers of NSAID's such as ibuprofen and fenoprofen, and likely adaptable to resolution of ketoprofen, include the method of Doyle et al, *Pharm. Technol.* 9(2), 28–32 (1985), which utilizes conversion of the racemate to its amide derivatives for effective resolution; and that of Wainer et al, *J. Chromatogr.* 284(1), 117–124 (1984), which utilizes conversion of the drug to 1-naphthalenemethylamide derivatives.

A method for derivatizing ketoprofen, fenoprofen and other nonsteroidal anti-inflammatory drugs with optically active amphetamine (α-methylbenzeneethanamide) has been described by Singh et al, *J. Chromatogr. Biomed. Appln.*, 378, 125–135 (1986). Those authors also provide a summary of the usual methods for resolving enantiomers, i.e. (1) by direct separation or chiral HPLC or GC (gas chromatographic) columns, or (2) by diastereoisomer formation, by reaction with an optically pure resolving agent, followed by chromatographic separation on an optically inactive column. Singh et al's method is a new version of the second approach, using optically active amphetamine as the resolving agent, followed by separation of the diastereoisomers by capillary gas chromatography with nitrogen-phsophorus detection. (The acid, now in optically pure form, could of course then be regenerated from the salt as is well-known.) The usual method in the art utilizes optically active α-methylbenzylamine and involves preparation of the diastereoisomeric NSAID-α-methylbenzylamide directly by means of a coupling agent (e.g. 1,1'-carbonyldiimidazole) or via the NSAID acid chloride (prepared with thionyl chloride).

More generally speaking, the S(+) isomer can be separated from racemic ketoprofen by preparing a salt of ketoprofen with an alkaloid or similar resolving agent such as cinchonidine, then separating the products by fractional crystallization from a solvent in which the dextrorotatory isomer is least soluble. The d-salt can then be acid cleaved to yield S(+) ketoprofen. Compare, for example, Alvarez, U.S. Pat. No. 3,637,767, issued Jan. 25, 1972, which relates to resolution of naproxen and related compounds; and Kaiser et al, *J. Pharm. Sci.* 65(2), 269–273 (1976), which relates to resolution of ibuprofen.

While S(+) ketoprofen may be conveniently obtained by resolution of racemic ketoprofen, it may also be possible to utilize a chemical or microbiological synthetic process which will provide the S(+) enantiomer directly. One such chemical process is described in Farge et al, U.S. Pat. No. 3,641,127, as already mentioned hereinabove. Another chemical process is provided by Schloemer, U.S. Pat. No. 4,542,237, which describes a process for preparing α-arylalkanoic acids utilizing novel α-hydroxy alkyl aryl ketals as intermediates. As taught in column 9 of the Schloemer patent, the process is advantageous in that the α-hydroxy ketal can be resolved by well-known methods and the optically active α-hydroxy ketal thus obtained can then be used in the subject process to ultimately afford the desired acid in optically pure form.

Alternatively, a microbiological process such as that described in SHELL INTERNATIONALE RESEARCH MAATSCHAPPIJ B.V.'s European Patent Apppln. No. 86 200987.5, published under No. 0 205215 on Dec. 17, 1986, may be employed. According to the European application, a pharmaceutically active compound of the type

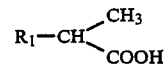

or a pharmaceutically active salt or ester thereof, which most preferably is naproxen or ibuprofen but which may be ketoprofen or various other NSAIDs, is prepared in sterospecific form by subjecting a compound of the formula

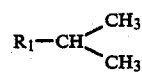

to the action of an appropriate microorganism. The desired acid is obtained having at least 70% by weight in the S-configuration. Preferably, a microorganism is selected such that the acid which is formed is at least 90% by weight in the S-configuration. Use of this method has afforded naproxen with enantiomeric distributions of 98.9% S and 1.1% R in one instance, and distributions of 99.5% S and 0.5% R in another. Processes of this type may be utilized to prepare S(+) ketoprofen for use in the present invention if the S(+) isomer can be obtained in sufficient purity [ideally, at least 90% by weight S(+) isomer.]

When S(+) ketoprofen is to be employed in the form of a pharmaceutically acceptable, antipyretically active salt thereof, such salt may be conveniently prepared by direct salification of S(+) ketoprofen by known methods. See, for example, deVincentiis, U.S. Pat. No. 4,440,787, which describes salts of (2',4'-difluoro-4-biphenyl)oxypropionic acid with metallic ions, such as sodium, potassium, magnesium and calcium, or with pharmaceutically acceptable organic bases, such as lysine, arginine and diethanolamine. Compare also Armitage et al, U.S. Pat. No. 4,501,727, issued Feb. 26, 1985, which describes the N-methyl-D-glucamine salt of flurbiprofen. Such a salt may not only be used in oral or rectal compositions, but, if sufficiently soluble in water, may be useful in the preparation of aqueous solutions of S(+) ketoprofen for parenteral injection.

From the foregoing description, one of ordinary skill in the art can easily ascertain the essential characteristics of the instant invention, and without departing from the spirit and scope thereof, can make various changes and/or modifications of the invention to adapt it to various usages and conditions. As such, these changes and/or modifications are properly, equitably and intended to be within the full range of equivalence of the following claims.

We claim:

1. The method of eliciting an onset-hastened and enhanced antipyretic response in a human mammal suffering from elevated body temperature and in need of such treatment, comprising administering to such organism a unit dosage onset-hastening/enhancing antipyretically effective amount of the S(+) ketoprofen enantiomer, and said enantiomer being substantially free of its R(−) ketoprofen antipode.

2. A method according to claim 1, wherein the weight ratio of S(+) ketoprofen to R(−) ketoprofen is greater than 9:1.

3. A method according to claim 2, wherein the weight ratio of S(+) ketoprofen to R(−) ketoprofen is greater than or approximately equal to 20:1.

4. A method according to claim 3, wherein the weight ratio of S(+) ketoprofen to R(−) ketoprofen is greater than 97:3.

5. A method according to claim 4, wherein the weight ratio of S(+) ketoprofen to R(−) ketoprofen is approximately equal to or greater than 99:1.

6. A method according to claim 1, comprising administering to such human mammal from about 6.0 to about 100 mg S(+) ketoprofen.

7. A method according to claim 1, comprising administering to such human mammal from about 12.5 to about 75 mg S(+) ketoprofen.

8. A method according to claim 1, comprising administering to such human mammal from about 25 to about 50 mg S(+) ketoprofen.

9. A method according to claim 2, comprising administering to such human mammal from about 6.0 to about 100 mg S(+) ketoprofen.

10. A method according to claim 2, comprising administering to such human mammal from about 12.5 to about 75 mg S(+) ketoprofen.

11. A method according to claim 2, comprising administering to such human mammal from about 25 to about 50 mg S(+) ketoprofen.

12. A method according to claim 3, comprising administering to such human mammal from about 6.0 to about 100 mg S(+) ketoprofen.

13. A method according to claim 3, comprising administering to such human mammal from about 12.5 to about 75 mg S(+) ketoprofen.

14. A method according to claim 3, comprising administering to such human mammal from about 25 to about 50 mg S(+) ketoprofen.

15. A method according to claim 4, comprising administering to such human mammal from about 6.0 to about 100 mg S(+) ketoprofen.

16. A method according to claim 4, comprising administering to such human mammal from about 12.5 to about 75 mg S(+) ketoprofen.

17. A method according to claim 4, comprising administering to such human mammal from about 25 to about 50 mg S(+) ketoprofen.

18. A method according to claim 5, comprising administering to such human mammal from about 6.0 to about 100 mg S(+) ketoprofen.

19. A method according to claim 5, comprising administering to such human mammal from about 12.5 to about 75 mg S(+) ketoprofen.

20. A method according to claim 5, comprising administering to such human mammal from about 25 to about 50 mg S(+) ketoprofen.

21. A method according to claim 1, wherein such human mammal is suffering from fever associated with a cold or flu.

22. A method according to claim 1, wherein the S(+) ketoprofen is orally administered to such human mammal.

23. A method according to claim 1, wherein the S(+) ketoprofen is rectally administered to such human mammal.

24. A method according to claim 1, wherein the S(+) ketoprofen is topically administered to such human mammal.

* * * * *